United States Patent
Uno et al.

(10) Patent No.: US 7,601,478 B2
(45) Date of Patent: Oct. 13, 2009

(54) BICYCLO COMPOUND, METHOD FOR PRODUCING FUSED AROMATIC COMPOUND USING THE SAME AND METHOD FOR FORMING FILM OF THE SAME

(75) Inventors: Hidemitsu Uno, Matsuyama (JP); Noboru Ono, Matsuyama (JP)

(73) Assignee: Canon Kabushiki Kaisha, Tokyo (JP)

( * ) Notice: Subject to any disclaimer, the term of this patent is extended or adjusted under 35 U.S.C. 154(b) by 718 days.

(21) Appl. No.: 10/543,382

(22) PCT Filed: Mar. 1, 2004

(86) PCT No.: PCT/JP2004/002498

§ 371 (c)(1),
(2), (4) Date: Jul. 26, 2005

(87) PCT Pub. No.: WO2004/078692

PCT Pub. Date: Sep. 16, 2004

(65) Prior Publication Data

US 2006/0142627 A1  Jun. 29, 2006

(30) Foreign Application Priority Data

Mar. 3, 2003 (JP) .............................. 2003-056143

(51) Int. Cl.
*C07C 15/12* (2006.01)
(52) U.S. Cl. .............................. 430/270.1; 430/270.11; 430/298; 430/321; 430/644; 257/40; 428/1.2
(58) Field of Classification Search ............. 585/25–27; 430/270.1–270.11, 298, 321, 644; 257/40; 428/1.2
See application file for complete search history.

(56) References Cited

U.S. PATENT DOCUMENTS 6,500,604 B1  12/2002  Dimitrakopoulos et al. . 430/322

(Continued)

FOREIGN PATENT DOCUMENTS

JP  2004-221318 A  8/2004

OTHER PUBLICATIONS

Rubin, M.B. (1985). "Recent Photochemistry of alpha-Diketones" in Photochemistry and Organic Synthesis, 129, Springer-Berlin/Heidelberg, pp. 1-56.*

(Continued)

*Primary Examiner*—Glenn A Caldarola
*Assistant Examiner*—Brian McCaig
(74) *Attorney, Agent, or Firm*—Fitzpatrick, Cella, Harper & Scinto (57) ABSTRACT

There is provided a method for producing highly purified fused aromatic ring compounds with high yield by a simpler method. A method for producing a fused aromatic ring compound comprising irradiating the bicyclo compound containing at least one bicyclo ring represented by formula (1) in a molecule with light to detach a leaving group X from a residual part to form an aromatic ring: wherein R1 and R3 each denotes a group to form an aromatic ring or a heteroaromatic ring which may be substituted, together with a group to which each thereof is bonded; R2 and R4 each denotes a hydrogen atom, an alkyl group, an alkoxy group, an ester group or a phenyl group; and X is a leaving group, which denotes a carbonyl group or —N=.

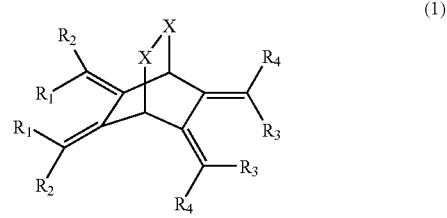

2 Claims, 5 Drawing Sheets

U.S. PATENT DOCUMENTS

| | | |
|---|---|---|
| 2003/0136964 A1 | 7/2003 | Afzali-Ardakani et al. .... 257/72 |
| 2003/0144562 A1 | 7/2003 | Afzali-Ardakani et al. .. 570/212 |
| 2004/0110093 A1 | 6/2004 | Afzali-Ardakani et al. |
| 2004/0119073 A1 | 6/2004 | Ardakani et al. |

OTHER PUBLICATIONS

Marcus W. Wright et al., "Transition Metal Mediated Exo Selective Diels-Alder Reactions: Preparation of 2-Cobalt-Substituted 1,3-Dienes Containing $C_2$ Symmetric 2,3-Dibenzobicyclo[2.2.2]octanedione Dioxime Equatorial Ligands and Their Use in Thermal and Lewis Acid Catalyzed 4+2 Cycloadditions", *J. Org. Chem.*, 1996, vol. 61, pp. 133-141.

Glen A. Russell et al., "Decarbonylation and Decarboxylation by Lithium in Hexamethylphosphoramide", *J. Org. Chem.*, vol. 43, No. 11, 1978, pp. 2242-2244.

Hans-Dieter Scharf et al., "Diensynthesen mit Dichlorvinylencarbonat", *Chem. Ber.*, 1972, vol. 105, pp. 564-574.

J. Strating et al., "Evidence for the Expulsion of bis-CO From Bridged α-Diketones", *Tetrahedron Letters*, 1969, No. 3, pp. 125-128.

Wyman R. Vaughan et al., "Studies in the Dibenzobicyclo[2.2.2]octadiene System", *J. Org. Chem.*, 1957, vol. 22, pp. 528-532.

Henrik Olsen et al., "Concerted Thermal Cycloreversion of Unsaturated Azo N-Oxides", *J. Am. Chem. Soc.*, 99(5), 1977, pp. 1524-1536.

H. Hart. et al, "Photochemical and Thermal Inertness of a Bicyclo[2.2.2]octadienone Diimine," 4 Chem. Commun. 126-27 (1974).

Peter T. Herwig et al., "A Soluble Pentacene Precursor: Synthesis, Solid-State Conversion into Pentacene and Application in a Field-Effect Transistor," 11(6) Adv. Mater. 480-83 (1999).

Ali Afzali et al., "High-Performance, Solution-Processed Organic Thin Film Transistors from a Novel Pentacene Precursor," 124 J. Am. Chem. Soc. 8812-13 (2002).

\* cited by examiner

BICYCLO COMPOUND, METHOD FOR PRODUCING FUSED AROMATIC COMPOUND USING THE SAME AND METHOD FOR FORMING FILM OF THE SAME

TECHNICAL FIELD

The present invention relates to novel bicyclo compounds, a method for producing highly purified fused aromatic compounds using the same. The present invention further relates to a method for forming a film of such a highly purified fused aromatic compound.

BACKGROUND ART

In the electronics field, non-linear optical properties, conductivity and semiconductivity of various organic compounds have been attracting attention, and various devices using organic substances have been developed actively. Phthalocyanine compounds, porphyrin compounds, fused polycyclic aromatic ring compounds such as polyacenes and pyrene, arylamine compounds, bisazo pigments and the like are known as typical examples of organic semiconductor compounds. Properties such as non-linear optical properties, electrical conductivity and semiconductivity, which are required for using these compounds as organic materials to form devices, largely depend on crystallinity and orientation of each of the materials, and it is important to use highly purified materials in order to fully exploit these properties. However, high purification of these materials has been difficult, because many of compounds having an extended π-conjugated system are susceptible to oxidation in air.

Fused aromatic ring compounds represented by pentacene have been receiving attention in recent years for their electrical conductivity, semiconductivity etc. However, it is very difficult to obtain pentacene of high purity due to its low solubility.

Particularly, it is necessary to form thin films of pentacene in order to use it for various devices, but thin film preparation using a vacuum process etc. increases the production cost. In recent years, there has been developed a method for producing pentacene precursor from a pentacene precursor using the reverse Diels-Alder reaction as a key reaction (WILLEY-VCH Verlag GmbH, "Advanced Materials", Vol. 11, No. 6, p. 480-483, 1999). However, the conversion to pentacene requires a high-temperature treatment of 170° C. or above and freed high mass components must be removed under a reduced pressure. Conversion to pentacene at a low temperature is also reported ("Journal of American Chemical Society", Vol. 124, p. 8812-8813, American Chemical Society, 2002), but there is a problem in the stability of the soluble precursor of pentacene.

DISCLOSURE OF THE INVENTION

Conventionally, highly purified fused aromatic ring compounds are difficult to obtain due to the low solubility thereof. Particularly, acene compounds have a low solubility and are difficult to purify, so a method for producing highly purified compounds has been demanded. Further, a vacuum process such as vacuum evaporation or sputtering is required for preparation of a film of a fused aromatic ring compound, so a simpler method has been demanded.

The present invention was made to solve these problems, and it is an object of the present invention to provide new bicyclo compounds to be used for obtaining highly purified fused aromatic ring compounds.

It is another object of the present invention to provide a method for producing a highly purified fused aromatic ring compound with high yield by a method simpler than the conventional ones.

It is a further object of the present invention to provide a method for easily forming films of highly purified fused aromatic ring compounds.

The inventors have found new bicyclo compounds having a specific structure. Specifically, they found that a leaving group is detached from such a bicyclo compound by light irradiation, and an aromatic ring is formed in the residual part to form a fused aromatic ring compound. Further, they found that the film of a bicyclo compound of a specific structure can easily be converted into a film of a fused aromatic ring compound by the photodecomposition reaction. The present invention has been made based on these findings.

Namely, the present invention provides a bicyclo compound containing at least one bicyclo ring represented by formula (1) in a molecule:

Formula (1)

wherein $R_1$ and $R_3$ each denotes a group to form an aromatic ring or a heteroaromatic ring which may be substituted, together with a group to which each thereof is bonded; $R_2$ and $R_4$ each denotes a hydrogen atom, an alkyl group, an alkoxy group, an ester group or a phenyl group; and X is a leaving group denoting a carbonyl group or —N=.

Further, the present invention provides a bicyclo compound represented by formula (1a):

Formula (1a)

wherein denotes an aromatic ring or a heteroaromatic ring which may be substituted or not; a, b and c each denotes an integer of 1 to 4; d denotes an integer of 0 to 4; $R_{31}$, $R_{32}$ and $R_{33}$ each denotes at least one hydrogen atom, alkyl group, alkoxy group, ester group, aryl group, aralkyl group, phenoxy group, cyano group, nitro group or halogen atom, which may be the same or different; and X is a leaving group denoting a carbonyl group or —N=.

Further, the present invention provides a method for producing a fused aromatic ring compound by irradiating the above bicyclo compound with light to detach a leaving group X from the residual part to form an aromatic ring.

Further, the present invention provides a method for forming a film of a fused aromatic ring compound by irradiating a film of the above bicyclo compound with light to detach a leaving group X from the residual part to form an aromatic ring.

Further, the present invention provides a method for forming a patterned film of a fused aromatic ring compound by writing a pattern on a film of the above bicyclo compound by light irradiation to detach a leaving group X from a residual part to form an aromatic ring.

Further, the present invention provides a method for producing a pentacene compound by photolytically decomposing 6,13-ethanopentacene-6,13-dione represented by formula (2):

Formula (2)

wherein $R_2$ and $R_4$ each denotes a hydrogen atom, an alkyl group, an alkoxy group, an ester group or a phenyl group; and $R_5$ to $R_{12}$ each denotes a hydrogen atom, an alkyl group, an alkoxy group, an aryl group, an aralkyl group, a phenoxy group, a cyano group, a nitro group, an ester group or a halogen atom, which may be the same or different.

Further, the present invention provides a method for forming a film of a pentacene compound by irradiating a film of 6,13-ethanopentacene-6,13-dione represented by formula (2) with light.

Further, the present invention provides a method for forming a patterned film of a pentacene compound by writing a pattern on a film of 6,13-ethanopentacene-6,13-dione represented by formula (2) by light irradiation.

The present invention also provides new bicyclo compounds usable for obtaining highly purified fused aromatic ring compounds.

Further, the present invention provides a method for producing highly purified fused aromatic ring compounds with high yield by a simpler method than conventional methods.

Further, the present invention provides a method for easily forming films of highly purified fused aromatic ring compounds.

BEST MODE FOR CARRYING OUT THE INVENTION

Hereinafter, the present invention is described in detail.

The present invention provides a method by which a fused aromatic ring compound having a low solubility can be produced simply and with high purity and a method by which a film of the fused aromatic ring compound having a low solubility can be easily formed, using a new bicyclo compound.

The bicyclo compound of the present invention is characterized by having at least one bicyclo ring represented by formula (1):

Formula (1)

In formula (1), $R_1$ and $R_3$ each denotes a group to form an aromatic ring or a heteroaromatic ring which may be substituted, together with a group to which each thereof is bonded.

The aromatic ring or heteroaromatic ring includes benzene ring, a naphthalene ring, an anthracene ring, a pyridine ring, a pyrrole ring or a thiophene ring; and the substituent includes an alkyl group such as methyl, ethyl or propyl, an aryl group such as phenyl or naphthyl, an aralkyl group such as benzyl or phenethyl, an alkoxy group such as methoxy or ethoxy, a phenoxy group, a carboxyl group, an ester group, a cyano group, a nitro group or a halogen atom such as fluorine, chlorine, bromine or iodine.

$R_2$ and $R_4$ each denote a hydrogen atom, an alkyl group such as methyl, ethyl or propyl, an alkoxy group such as methoxy or ethoxy, an ester group or a phenyl group.

X is a leaving group denoting a carbonyl group or —N═. Further, X—X preferably is —CO—CO— or —N═N— group.

Further, the present invention provides a method for producing a fused aromatic ring compound utilizing the formation of an aromatic ring by a residual part by irradiating the compound of formula (1) with light to detach the leaving group X from the residual part.

Further, the present invention provides a method for forming a film of a fused aromatic ring compound utilizing the formation of an aromatic ring by a residual part by irradiating the compound of formula (1) with light to detach the leaving group X from the residual part.

The bicyclo compound of formula (1) is irradiated with light to release two molecules of carbon monoxide or nitrogen gas as a leaving group, to allow the residual part to form an aromatic ring, thereby being converted to a fused aromatic ring compound.

Here, the wavelength of the light with which the compound of formula (1) is irradiated may be within the absorption wavelength range of the compound of formula (1), preferably in a longer wavelength range. A light source can be selected includes from a tungsten lamp, a halogen lamp, a metal halide lamp, a sodium lamp, a xenon lamp, a high-pressure mercury-vapor lamp, a low-pressure mercury-vapor lamp, various laser light and the like.

Further, the light source to be used is preferably a light source having a light emission intensity of 300 W or more. Too weak intensity may cause side reaction.

The reaction can provide a fused aromatic ring compound when the compound of formula (1) is dissolved or suspended in a solvent, and can form a film of a fused aromatic ring compound when the compound of formula (1) is in a film state such as a coating film or an evaporated film.

The solvent for the reaction in which light irradiation is performed includes methanol, ethanol, butanol, acetone, methyl ethyl ketone, methyl isobutyl ketone, cyclohexanone, hexane, heptane, cyclohexane, tetrahydrofuran, dioxane, diethyl ether, isopropyl ether, dibutyl ether, toluene, xylene, 1,2-dimethoxy ethane, chloroform, ethylene chloride, dimethyl sulfoxide, N-methylpyrrolidone, chlorobenzene, dichlorobenzene, trichlorobenzene or the like.

The reaction temperature of the light irradiation reaction may be selected in a wide range considering properties such as stability and solubility of the solvent capable of dissolving the compound of formula (1). Preferably, the reaction temperature is in a range from the boiling point to the freezing point of the solvent. Further, the solvent is preferably purged with an inert gas. When a film of a wide area is irradiated with light, uniformity of the light irradiation must be considered. When irradiation is done through a mask, care must be taken for close contact between the mask and the film. Further, direct patterning by laser light or the like is possible.

A preferable example of the present invention provides a 6,13-ethanopentacene-6,13-dione compound represented by formula (2):

Formula (2)

wherein $R_2$ and $R_4$ each denotes a hydrogen atom, an alkyl group such as methyl, ethyl or propyl, an alkoxy group such as methoxy or ethoxy, an ester group or a phenyl group.

$R_5$ to $R_{12}$ each denotes a hydrogen atom, an alkyl group such as methyl, ethyl or propyl, an alkoxy group such as methoxy or ethoxy, an aryl group such as phenyl or naphthyl, an aralkyl group such as benzyl or phenethyl, a phenoxy group, a cyano group, a nitro group, an ester group or a halogen atom such as fluorine, chlorine, bromine or iodine, which may be the same or different.

Further, a method for producing a preferable fused aromatic ring compound using a compound of formula (2) is to irradiate 6,13-ethanopentacene-6,13-dione represented by formula (2) with light to release two molecules of carbon monoxide being a leaving group, thus produce pentacene as shown by reaction scheme (3):

Reaction scheme (3)

A method for forming a preferable film of a fused aromatic ring compound using a compound of formula (2) is to irradiate a film of 6,13-ethanopentacene-6,13-dione represented by formula (2) with light to release two molecules of carbon monoxide being a leaving group, thus forming a film of pentacene as represented by reaction scheme (3).

Further, a method for forming a preferably patterned film of a fused aromatic ring compound using a compound of formula (2) is to directly write a pattern on a film of 6,13-ethanopentacene-6,13-dione represented by formula (2) with light to release two molecules of carbon monoxide being a leaving group, thus forming a patterned film of pentacene.

A typical synthetic route of the bicyclo compound of the present invention is shown below with an example synthesis of 6,13-ethanopentacene-6,13-dione, a compound example (6).

The synthetic route comprises the steps as shown by reaction scheme (4).

Reaction scheme (4)

Namely, a tetraene compound (1) reacts with two molecules of benzyne (2) by addition to produce an adduct (3); the adduct (3) is subjected to dehydrogenation reaction to produce an ethylene adduct (4); the compound (4) is oxidized to a diol (5) by an oxidizing agent such as osmium tetroxide; and the diol (5) is oxidized to a ketone, thereby 6,13-ethano-pentacene-6,13-dione (6) is provided. The compound (6) is easily decomposed by light irradiation to pentacene (7). Note that the compound. (6) can also be synthesized by direct addition of ethylene to pentacene.

Further, an alternative step shown in the bottom of reaction scheme (4) is also possible. Specifically, the compound (6) can be obtained by treating a compound (9), which is prepared by adding dichloroethylene carbonate (8) to pentacene (7), with alkali such as KOH or the like.

An asymmetric bicyclo compound can be obtained according to a route represented by reaction scheme (5), in which an equivalent amount of benzyne is added to the tetraene compound (1) to obtain a diene (10), to which benzyne (11) having a different substituent is added, and subsequently treated in the same manner as in formula (4) to obtain a asymmetric bicyclo compound (15).

Reaction scheme (5)

-continued

13

14

-continued

15

Further, a compound (20) which has two bicyclo rings in a molecule can be synthesized through a route using dibenzyne (16) as shown in reaction scheme (6). As a modification of this reaction, a compound (21) which has three bicyclo rings can be synthesized, where dibenzyne (16) and the compound (10) are reacted in equivalent amounts, an equivalent amount of dibenzyne (16) is added to the above addition product, and then the compound (1) is added, which is subsequently reacted with the compound (10) and converted to a ketone via an alcohol in the same manner as in formula (4). When dibenzyne (16) and the compound (10) are reacted in the equivalent amounts, the reaction product is reacted with the compound (1), then the reaction product is reacted with one-half equivalent amount of dibenzyne (16) and converted to a ketone via an alcohol in the same manner as in formula (4), a compound having four bicyclo rings can be obtained.

Reaction scheme (6)

These reaction routes are only a part of examples, and the route to obtain a compound of formula (1) is not limited to them.

The bicyclo compound of the present invention preferably includes a compound represented by formula Formula (1a)

In the formula,

Ⓐ, Ⓑ or Ⓒ denotes an aromatic ring or a heteroaromatic ring which may be substituted.

In the formula, a, b and c each denotes an integer of 1 to 4, and d denotes an integer of 0 to 4.

When the aromatic ring or heteroaromatic ring has no substituent, $R_{31}$, $R_{32}$ and $R_{33}$ each denotes a hydrogen atom. When the aromatic ring or heteroaromatic ring has any substituent, $R_{31}$, $R_{32}$ and $R_{33}$ each denotes an alkyl group, an alkoxy group, an ester group, an aryl group, an aralkyl group, a phenoxy group, a cyano group, a nitro group or a halogen atom, which may be one or more and may be the same or different.

X is a leaving group being a carbonyl group or —N═, with the proviso that X—X is —CO—CO— or —N═N— group.

Examples of bicyclo compounds used in the present invention are shown in Tables 1-4. They have one bicyclo ring and a carbonyl group as X.

TABLE 1

TABLE 1-continued

TABLE 2

TABLE 2-continued

| Compound No. | (structure with R1, R2) | (structure with R3, R4) |
|---|---|---|
| 32 | 2-methyl naphthalene with H3C | 2-methyl naphthalene with CH3 |
| 33 | 2,3-dimethyl naphthalene with H3C, H3C | 2,3-dimethyl naphthalene with CH3, CH3 |
| 34 | tetrafluoro naphthalene | tetrafluoro naphthalene |
| 35 | phenyl-naphthalene | naphthalene-phenyl |
| 36 | PhH2C-anthracene | anthracene-CH2Ph |

TABLE 3

| Compound No. | (structure with R1, R2) | (structure with R3, R4) |
|---|---|---|
| 37 | H3CO2C-anthracene-anthracene | anthracene-anthracene-CO2CH3 |
| 38 | H3CO-naphthalene-naphthalene | naphthalene-naphthalene-OCH3 |
| 39 | trifluoro naphthalene | naphthalene |
| 40 | NC, NC-naphthalene | naphthalene |

TABLE 3-continued

| Compound No. | (R1, R2 structure) | (R3, R4 structure) |
|---|---|---|
| 41 | 2,3-dimethyl-6,7-dimethylnaphthalene | naphthalene |
| 42 | 6,7-dimethoxy-2,3-dimethylnaphthalene | 6,7-dicyano-2,3-dimethylnaphthalene |
| 43 | naphthalene | anthracene |
| 44 | pentacene | 2,3-difluoro |

TABLE 4

| Compound No. | (R1, R2 structure) | (R3, R4 structure) |
|---|---|---|
| 45 | 2,3-dicyano-6,7-dimethylanthracene | 6,7-dicyano-2,3-dimethylnaphthalene |
| 46 | octafluoroanthracene-dimethyl | tetrafluoronaphthalene-dimethyl |
| 47 | anthracene-dimethyl | 2,3,6,7-tetramethylnaphthalene |
| 48 | anthracene | anthracene |
| 49 | octafluoroanthracene-dimethyl | octafluoroanthracene-dimethyl |

TABLE 4-continued

| Compound No. | |
|---|---|
| 50 | (structure) |
| 51 | (structure) |

TABLE 5

| Compound No. | |
|---|---|
| 52 | (structure) |
| 53 | (structure) |
| 54 | (structure) |
| 55 | (structure) |

Example compounds having two or three bicyclo rings are the above compound (20) or (21).

Further, the same substituents as $R_2$ $R_4$ and $R_5$ to $R_{12}$ represented in formula (1) can be selected for the compounds (20) and (21).

EXAMPLES

The present invention is not limited to the examples shown below.

Example 1

Synthesis of compound (3)

5,6,7,8-tetramethylidenebicyclo[2,2,2]oct-2-ene (1) (12 mmol, 1.91 g) and isoamyl nitrite (75 mmol, 10.0 ml) were dissolved in 80 ml of THF (tetrahydrofuran) in a reaction vessel, and refluxed with heating. A solution in which anthranilic acid (91 mmol, 12.5 g) was dissolved in 100 ml of THF was slowly added to the reaction dropwise using a dropping funnel. After the dropping, heating and stuffing were continued until all raw materials are consumed. After that, an aqueous sodium hydroxide solution was added to the reaction and stirring was continued. Then the reaction solution was extracted with hexane, and the resultant organic layer was washed with water and saturated saline, dried over anhydrous sodium sulfate and then concentrated to obtain a crude product. The product was purified by silica gel column chromatography (hexane) to obtain the compound (3). The yield was 2.66 g and 72%.

Molecular formula: $C_{24}H_{20}$ (308.42)
Shape: White crystal
$^1$H NMR (CDCl$_3$) δ=7.10 (4H, s), 6.85 (4H, -J=3.41), 4.29 (2H, t, J=3.41), 3.60 (8H, s) [270 MHz]
$^{13}$C NMR (CDCl$_3$) δ=140.179, 139.254, 134.241, 128.715, 125.858, 54.197, 33.164 [67.8 MHz]
Mass spectrum (FAB) m/z: 308 (M+: 22)
Elemental analysis: Calcd (%) C=93.46, H=6.54.
Found (%) C=93.54, H=6.68.

Synthesis of Compound (4)

The compound (3) (4.02 mmol, 1.24 g) was charged into a reaction vessel and dissolved in 50 ml of chloroform. This solution was added with DDQ (2,3-dichloro-5,6-dicyano-1,4-benzoquinone) (8.04 mmol, 1.80 g) and stirred for 2 hours. A saturated aqueous sodium bicarbonate solution was added to the resultant solution and shaken. The resultant organic layer was washed with water and saturated saline, dried over anhydrous sodium sulfate and then concentrated under reduced pressure to obtain a crude product. The product was purified by silica gel column chromatography (10% ethyl acetate/hexane) to obtain the compound (4).

Yield 1.20 g (98%)
Molecular formula: $C_{24}H_{16}$ (304.38)
Melting point: 277.2° C.
Shape: White crystal
$^1$H NMR (CDCl$_3$) δ=7.72 (4H, s), 7.69 (4H, m), 7.37 (4H, m), 7.04 (2H, q, J=3.42, 0.98), 5.32 (2H, m) [270 MHz]
$^{13}$C NMR (CDCl$_3$) δ=142.13, 138.24, 131.68, 127.42, 125.52, 121.23, 50.15 [67.8 MHz]
Infrared absorption spectrum (KBr) cm$^{-1}$: 3054, 2973
Mass spectrum (DIEI) m/z: 304 (M+: 100), 278 (13)
Elemental analysis: Calcd (%) C=94.70, H=5.30.
Found (%) C=94.36, H=5.58.

Synthesis of Compound (5)

NMO (N-methylmorpholine-N-oxide).H$_2$O (5.60 mmol, 0.78 g) and a stirring bar were put in a 1 L round bottomed flask, and purged with argon.

To the flask, 500 ml of acetone, OsO$_4$ (0.10 mmol, 5 ml) and the compound (4) (4.11 mmol, 1.25 g) were added in this order, and a stopper was plugged into the flask. The mixture was vigorously stirred for 32 hours while maintained at room temperature. The resultant mixture was added with an aqueous solution of Na$_2$S$_2$O$_4$ (0.6 g), stirred for 10 minutes, filtered through Celite, and the mother liquor was extracted with ethyl acetate. The resultant organic layer was washed with water and saturated saline, dried over anhydrous sodium sulfate and then concentrated under reduced pressure to obtain the compound (5) as a white crystal.

Yield 1.36 g (98%)
Molecular formula: $C_{24}H_{16}O_2$ (338.40)
Melting point: 299.8° C.
Shape: White crystal
$^1$H NMR (CDCl$_3$) δ=7.85 (2H, s), 7.80 (8H, m), 7.43 (4H, m), 4.66 (2H, s), 4.22 (2H, s) [270 MHz]
$^{13}$C NMR (CDCl$_3$) δ=137.349, 135.876, 132.722, 127.574, 125.876, 125.813, 125.220, 123.324, 68.411, 51.187 [100.4 MHz]
Infrared absorption spectrum (KBr) cm$^{-1}$: 3432.67, 370.68 (OH)
Mass spectrum (FAB) m/z: 339 (M+: 4)
Elemental analysis: Calcd (%) C=62.15, H=4.69.
Found (%) C=62.01, H=4.75.

Synthesis of Compound (6)

Dry DMSO (dimethyl sulfoxide) (132 mmol, 9.4 ml) and 69 ml of dry-CH$_2$Cl$_2$ were charged into a three-necked reaction vessel under an inert gas atmosphere, and cooled to −60° C. with an acetone/liquid nitrogen bath. To the mixture, 119 mmol (16.5 ml) of anhydrous trifluoroacetic acid was slowly dropped and stirred for 10 minutes, while maintaining the temperature of the liquid at −60° C. Then, to the resultant mixture, the compound (5) (3.81 mmol, 1.29 g) dissolved in a minimum amount of dry DMSO was slowly dropped and stirred for 15 hours. To the mixture, triethylamine (275 mmol, 20.7 ml) was dropped and stirred for 1.5 hours, while maintaining the temperature of the liquid at −60° C. The reaction solution was slowly poured into 2M HCl (200 ml) and was extracted with CH$_2$Cl$_2$. The resultant organic layer was washed with deionized water and saturated saline, dried over anhydrous sodium sulfate and then concentrated under reduced pressure to obtain a crude product, to which ethyl acetate was added. The resultant insoluble material was collected by filtration to obtain the compound (6).

Yield 0.55 g (43%)
Molecular formula: $C_{24}H_{14}O_2$ (334.37)
Melting point: 318-323
Shape: Yellow crystal
$^1$H NMR (CDCl$_3$) δ=7.94 (4H, s), 7.84 (4H, m), 7.52 (4H, m), 5.31 (2H, s) [270 MHz]
$^{13}$C NMR (CDCl$_3$) δ=185.165, 133.585, 131.851, 127.862, 127.017, 125.364, 60.603 [67.8 MHz]
Infrared absorption spectrum (KBr) cm$^{-1}$: 1754.90, 1735.62 (C=O)
Mass spectrum (DIEI) m/z: 335 (M+: 4)
Elemental analysis: Calcd (%) C=86.21, H=4.22.
Found (%) C=86.41, H=4.40.

Figure 1:
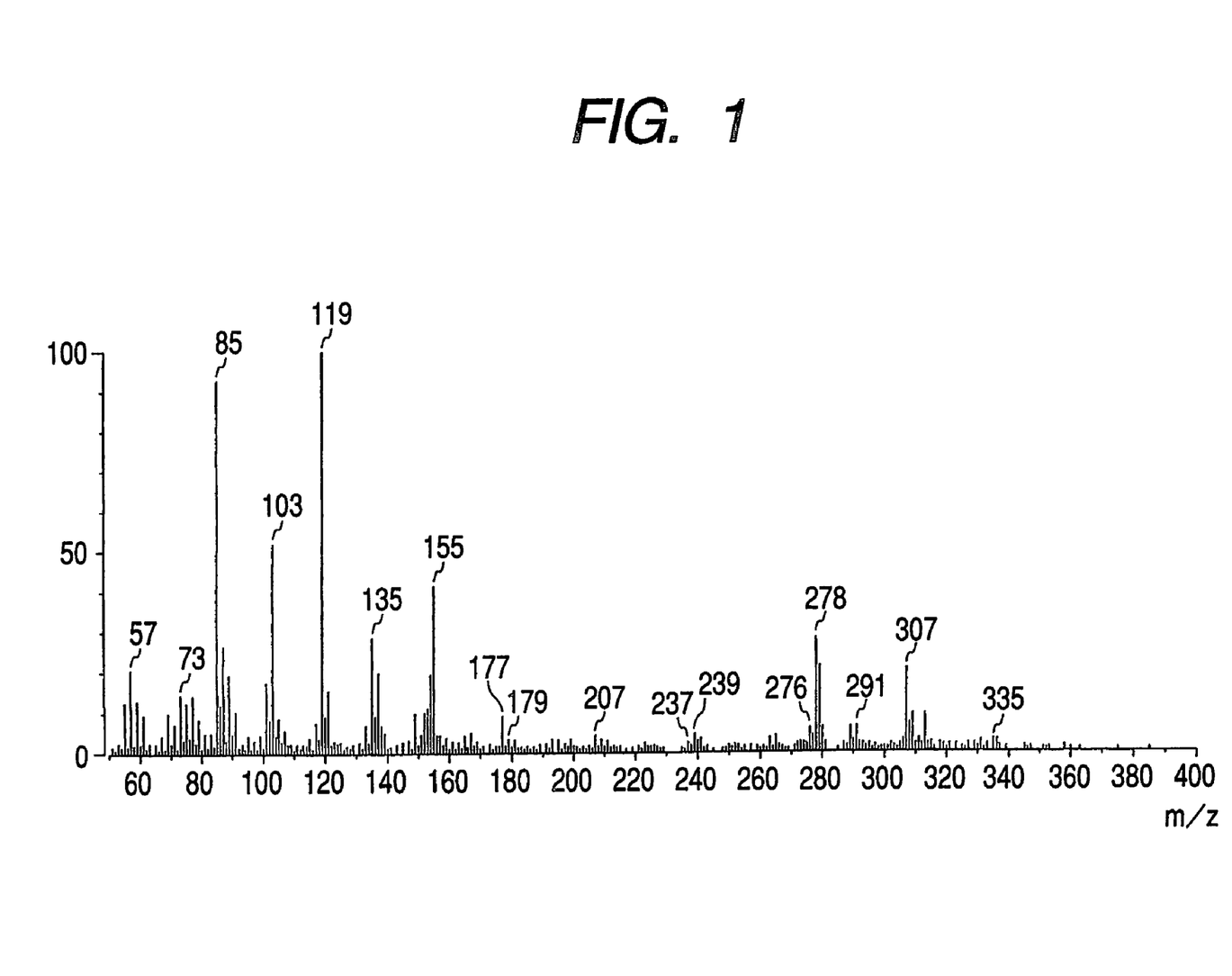
FIG. 1 shows a mass spectrum of compound (6) in Example 1.
Figure 2:
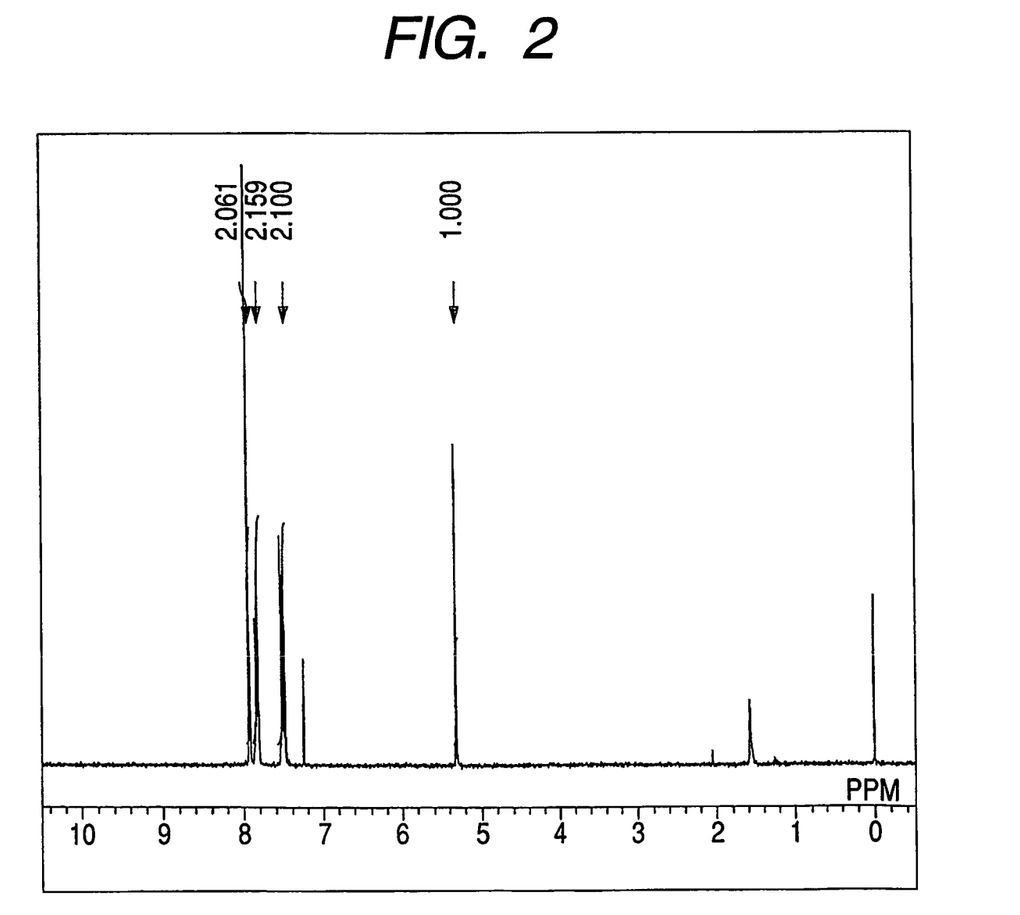
FIG. 2 shows a proton NMR spectrum (270 MHz) of compound (6) in Example 1.
Figure 3:
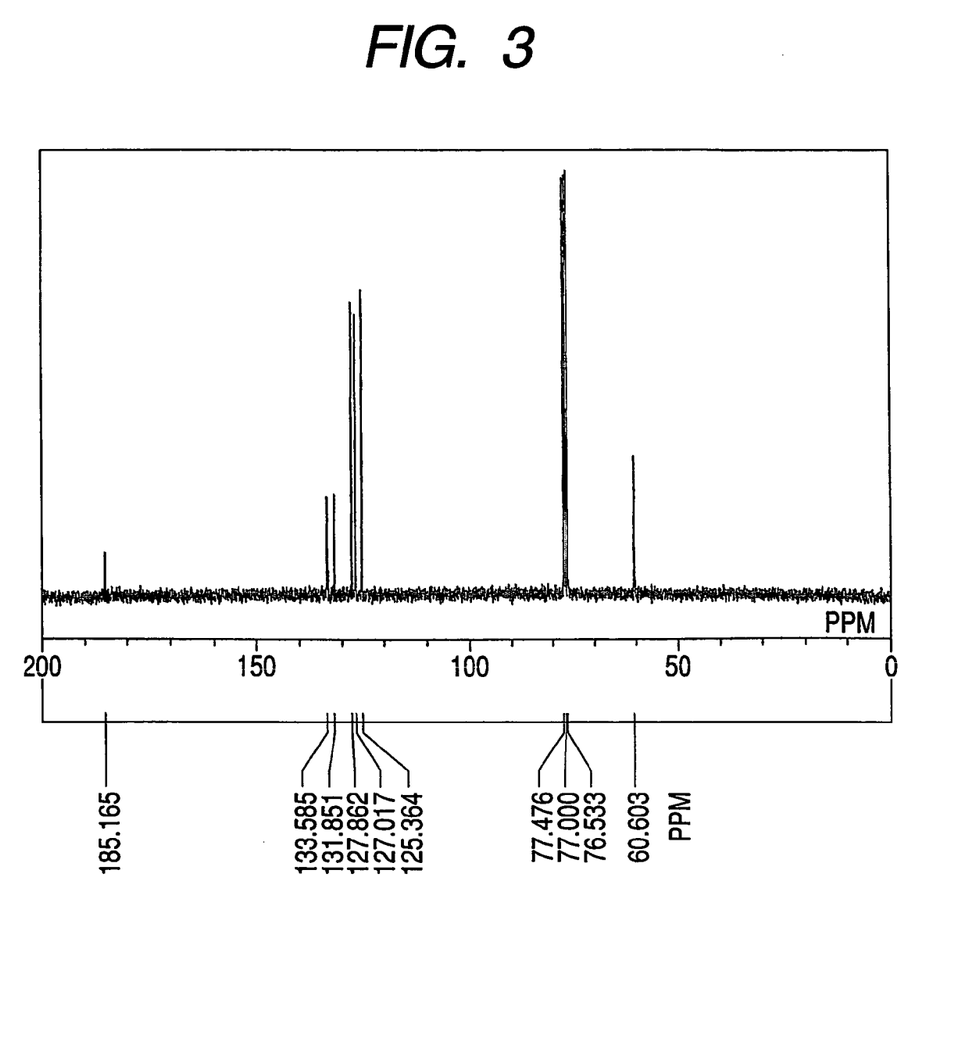
FIG. 3 shows a carbon 13 NMR of compound (6) in Example 1.
Figure 4:
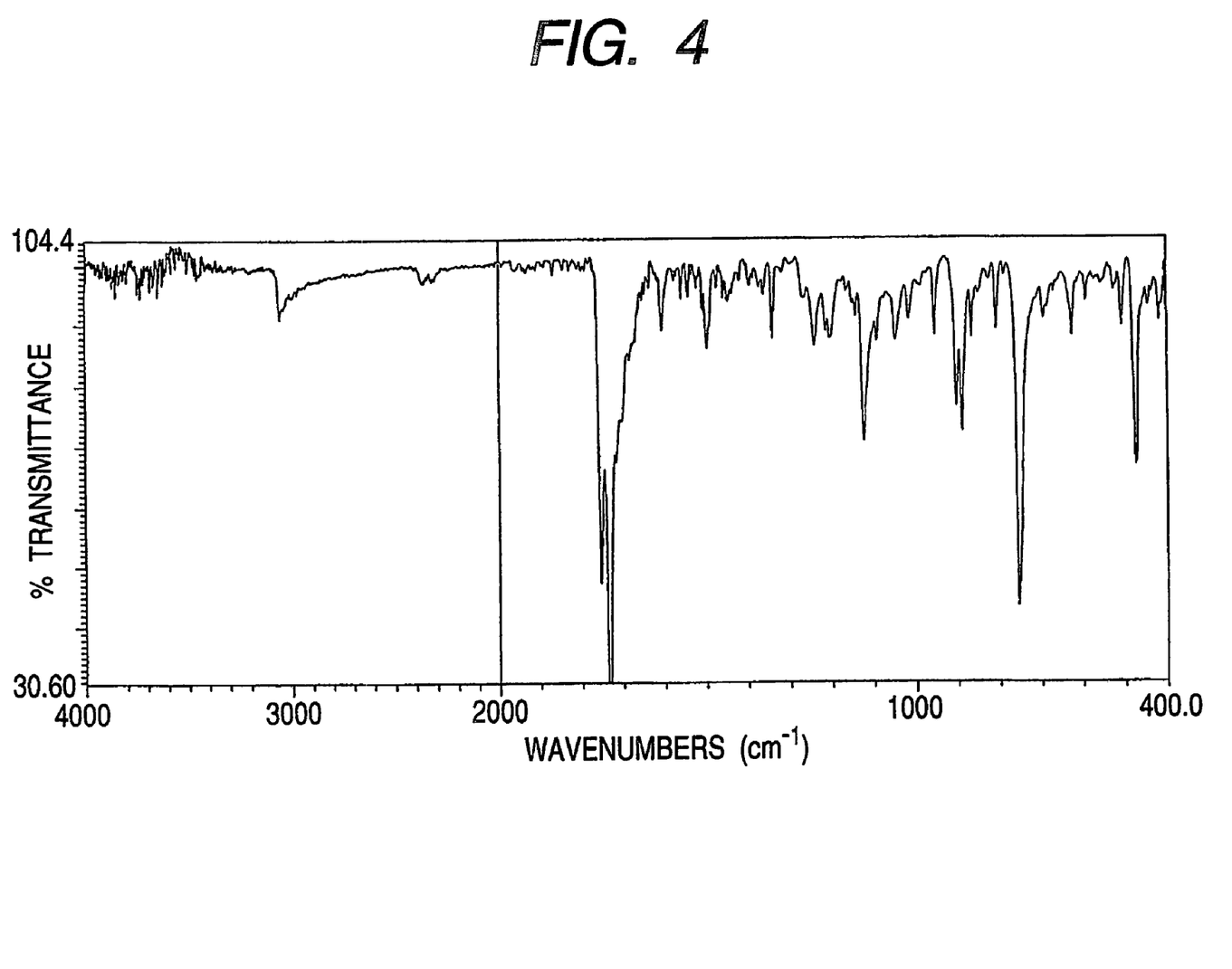
FIG. 4 shows an IR spectrum (KBr pellet method) of compound (6) in Example 1.
Figure 5:
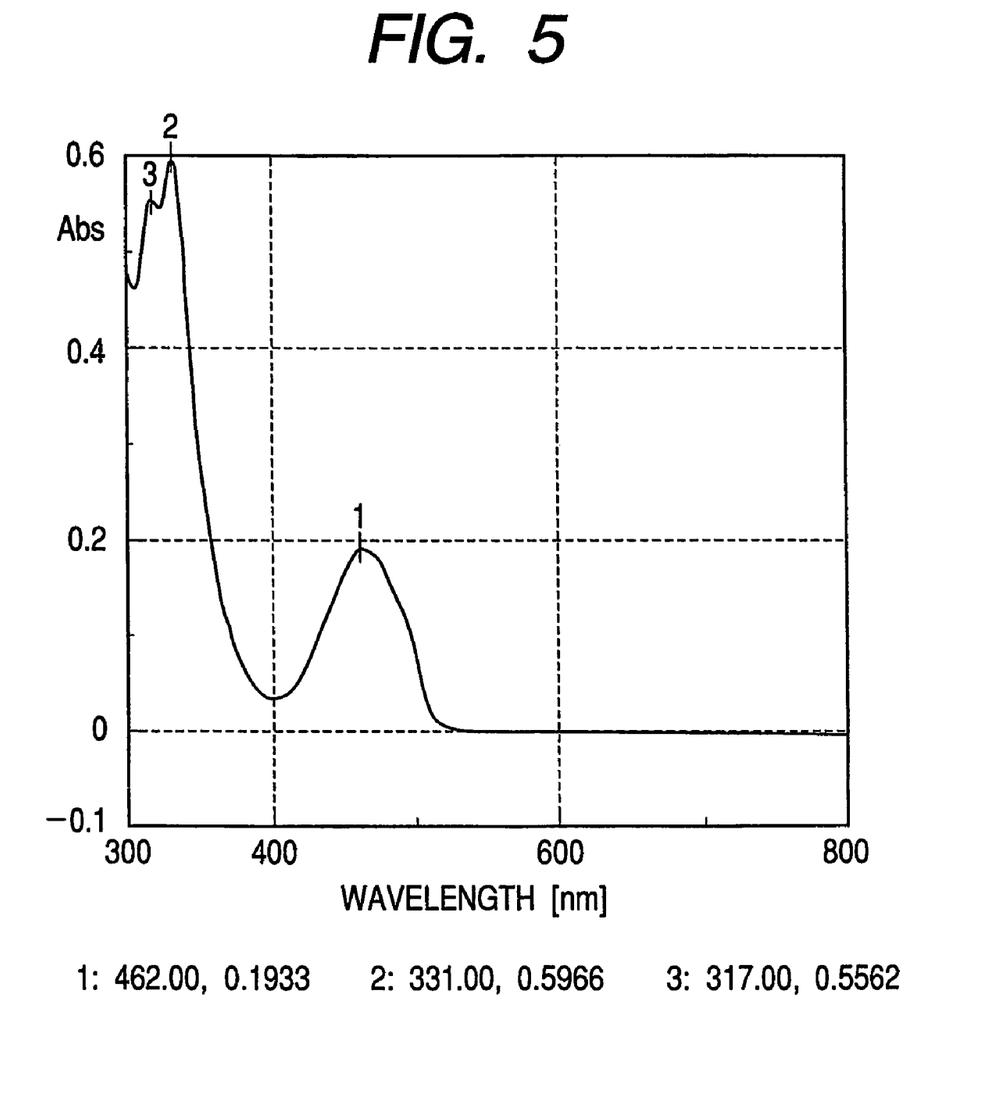
FIG. 5 shows a UV-VIS absorption spectrum of compound (6) in Example 1.

FIG. 1 shows the mass spectrum of compound (6) in Example 1; FIG. 2 shows the proton NMR spectrum (270 MHz) of compound (6) in Example 1; FIG. 3 shows the carbon 13 NMR of compound (6) in Example 1; FIG. 4 shows the IR spectrum (KBr pellet method) of compound (6) in Example 1; and FIG. 5 shows the UV-VIS absorption spectrum of compound (6) in Example 1.

Example 2

In a Pyrex (registered trade name) glass cell, 0.005 g of the compound (6) was dissolved in 2 ml of chloroform. The solution was sufficiently degassed and then irradiated with the metal halide lamp at room temperature. Blue crystals were precipitated after several minutes. They were collected by filtration to obtain pentacene (7).

Yield 0.004 g (96%)
Molecular formula: $C_{22}H_{14}$ (278.35)
Shape: Dark blue crystal
Infrared absorption spectrum (KBr) cm$^{-1}$: 468.14, 731.85, 906.38
Mass spectrum (EI) m/z: 278 (M+: 73)
Elemental analysis: Calcd (%) C=94.93, H=5.07.
Found (%) C=94.80, H=5.15.

Example 3

A 1% by weight solution of the compound (6) in dichloromethane was prepared. The solution was spin cast on a glass substrate to form a film having a thickness of 60 nm. The film was irradiated with light for 5 minutes by using a xenon lamp. The coating film immediately changed from pale yellow to blue. After the irradiation, the coating film did not come off even when immersed in chloroform. The UV absorption spectrum revealed the formation of pentacene.

Example 4

A 1% by weight solution of the compound (6) in dichloromethane was prepared. The solution was spin cast on a glass substrate to form a film having a thickness of 50 nm. The film was patterned using a dye laser of 460 nm. The coating film irradiated with the laser light immediately changed from pale yellow to blue. When the coating film was immersed in chloroform after the irradiation, the non-irradiated part dissolved and the part irradiated with the laser light remained as a blue pattern. The UV absorption spectrum of this part revealed the formation of pentacene.

Comparative Example 1

A glass tube with a diameter of 5 mm was charged with 0.005 g of the compound (4) and placed in an oil bath of 250° C. The content in the tube immediately changed to dark blue. After cooling, the content was thoroughly washed with chloroform and the remained crystal was separated by filtration. The yield was 0.003 g, 66%.

The invention claimed is:

1. A method for forming a patterned film of a pentacene compound comprising:
   writing a pattern on a film of 6,13-ethanopentacene-6,13-dione represented by formula (2) by light irradiation; and
   removing a part of the film not exposed by the light irradiation using chloroform, so that only the pattern written by the light irradiation remains:

(2)

wherein each of $R_2$ and $R_4$ denotes a hydrogen atom, an alkyl group, an alkoxy group, an ester group or a phenyl group; and each of $R_5$ to $R_{12}$ denotes one or more substituents selected from the group consisting of a hydrogen atom, an alkyl group, an alkoxy group, an aryl group, an aralkyl group, a phenoxy group, a cyano group, a nitro group, an ester group and a halogen atom.

2. The method according to claim 1, wherein the 6,13-ethanopentacene-6,13-dione is represented by formula (6):

(6)

* * * * *